United States Patent [19]
Failla et al.

[11] Patent Number: 5,368,600
[45] Date of Patent: Nov. 29, 1994

[54] STEERABLE BULLDOG CLAMP APPLIER

[75] Inventors: Stephen J. Failla, Cincinnati; Roger L. Hildwein, Loveland; Peter Lau, Cincinnati, all of Ohio

[73] Assignee: Ethicon, Inc., Somerville, N.J.

[21] Appl. No.: 96,587

[22] Filed: Jul. 23, 1993

[51] Int. Cl.$^5$ ............................................. A61B 17/04
[52] U.S. Cl. .................... 606/139; 606/142; 606/205; 606/207
[58] Field of Search .................. 606/139, 142, 205–211

[56] References Cited

U.S. PATENT DOCUMENTS

| | | | |
|---|---|---|---|
| 2,316,297 | 4/1943 | Southerland et al. | 606/139 |
| 4,706,668 | 11/1987 | Backer | 128/325 |
| 5,147,373 | 9/1992 | Ferzli | 606/148 X |
| 5,147,378 | 9/1992 | Markham | 606/206 |
| 5,258,007 | 11/1993 | Spetzler et al. | 606/139 X |

OTHER PUBLICATIONS

Codman & Shurtleff Product Catalogue, 1980, Codman & Shurtleff, Inc.
Solos Endoscopy Catalogue, Published by Birtcher, 1992.
Vascu-Statt ®, Published by Scanlon International, Inc., 1991.

*Primary Examiner*—Peter A. Aschenbrenner

[57] ABSTRACT

An applier for applying a bulldog clamp endoscopically, and the combination of such an applier with a bulldog clamp, is disclosed. The applier has an endoscopic portion and a handle portion. The handle portion can be manipulated to open and close gripping arms of the applier at the distal end of the endoscopic portion to correspondingly open and close the clamping jaws of the bulldog clamp. The principle feature of the invention is the ability to pivot the clamp while it is gripped within the gripping arms of the applier without the necessity of using another instrument or adjacent bodily tissue. Furthermore, it is possible to perform this pivoting movement from the proximal end of the applier, therefore enabling a surgeon to pivot the clamp from outside the body during endoscopic surgery. The preferred means for achieving pivoting movement includes the combination of a cantilevered spring mounted on one of the arms of the applier which biases the clamp off center from the longitudinal axis of the applier, and a guiding tube fitted over the endoscopic portion for steering the off-centered clamp. This steering function can be performed when the steering tube is moved distally to contact the clamp. The surgeon can then control the degree of pivoting movement by controlling the degree to which he advances the steering tube against the clamp.

19 Claims, 12 Drawing Sheets

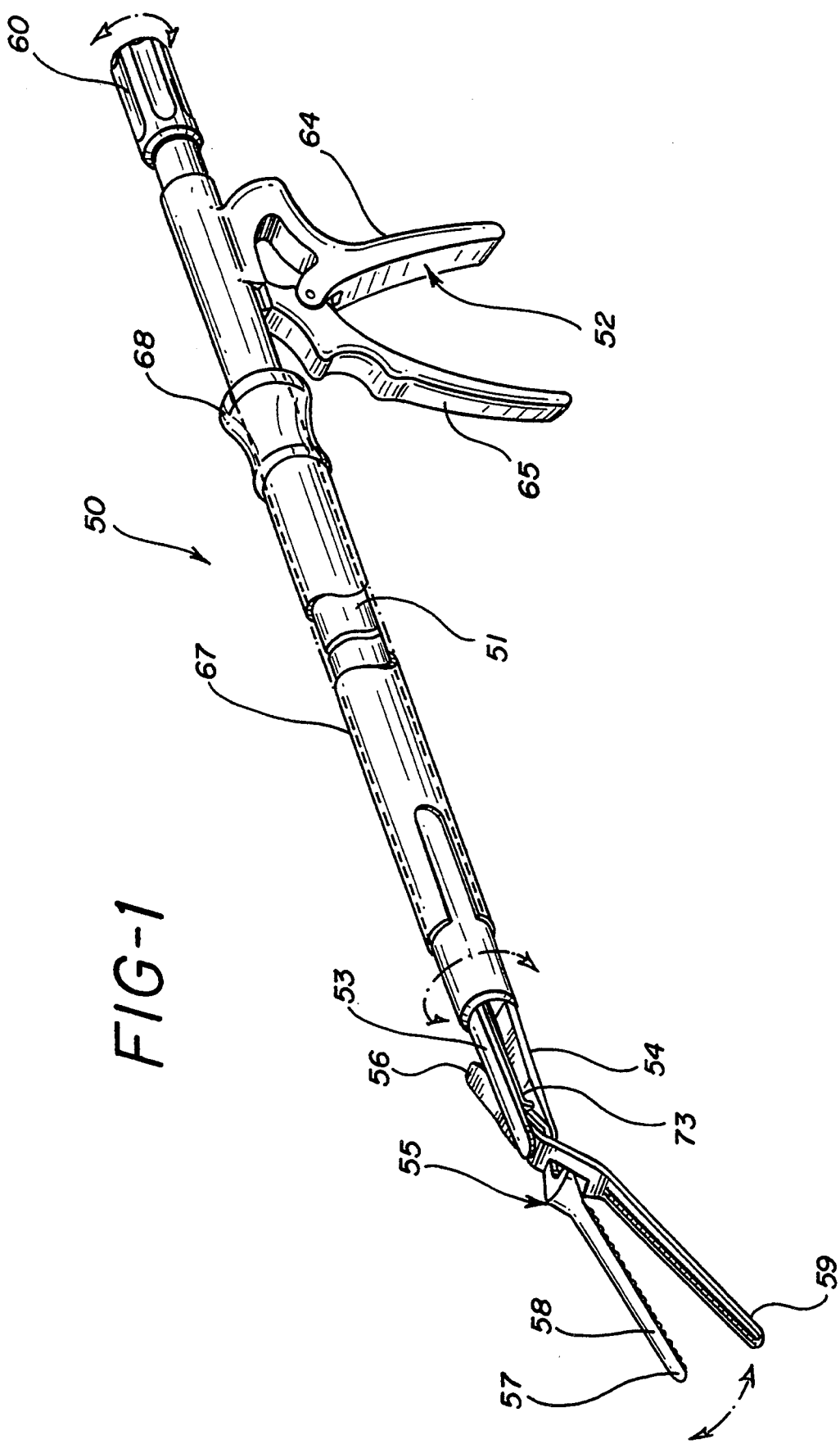

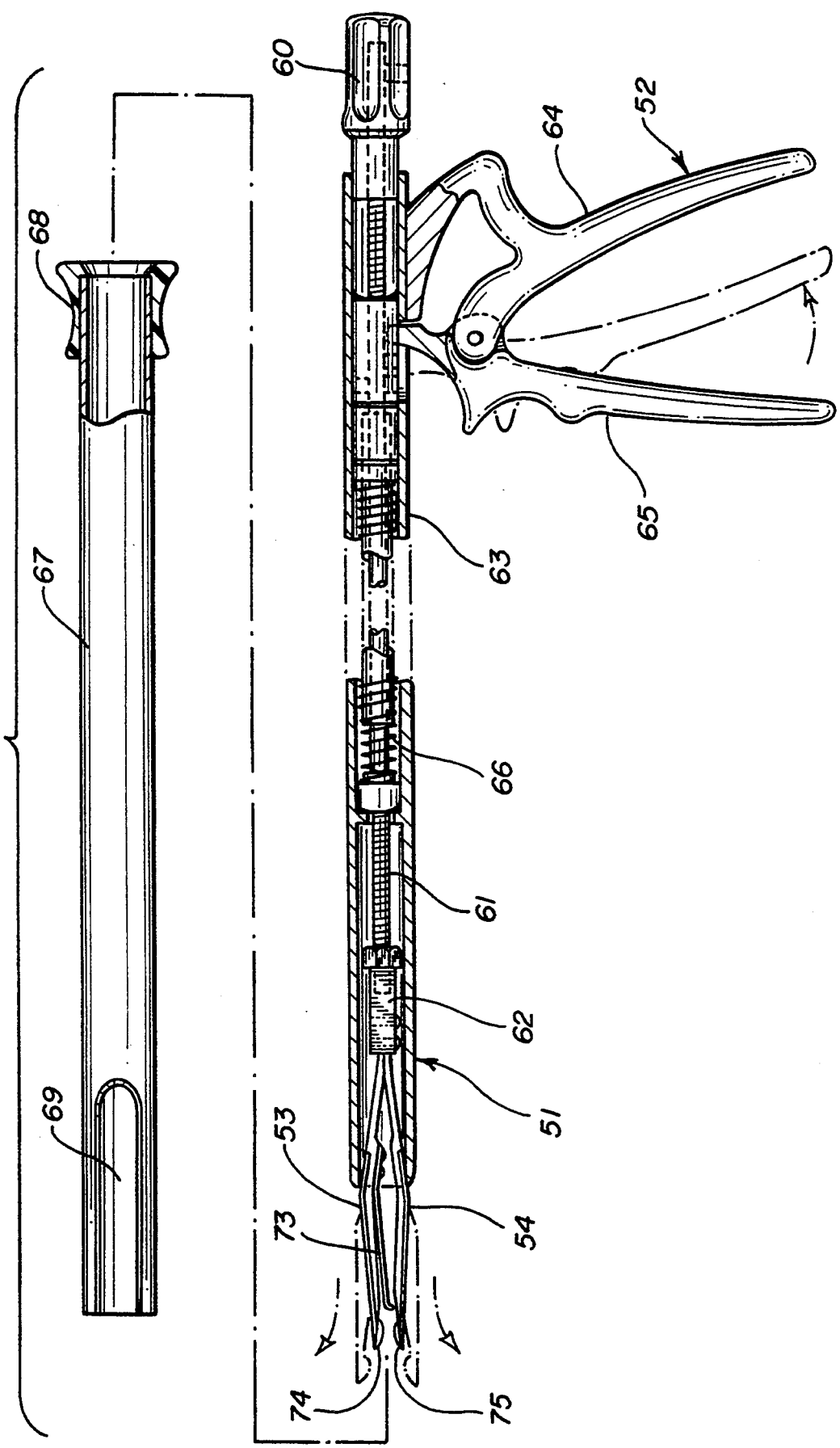

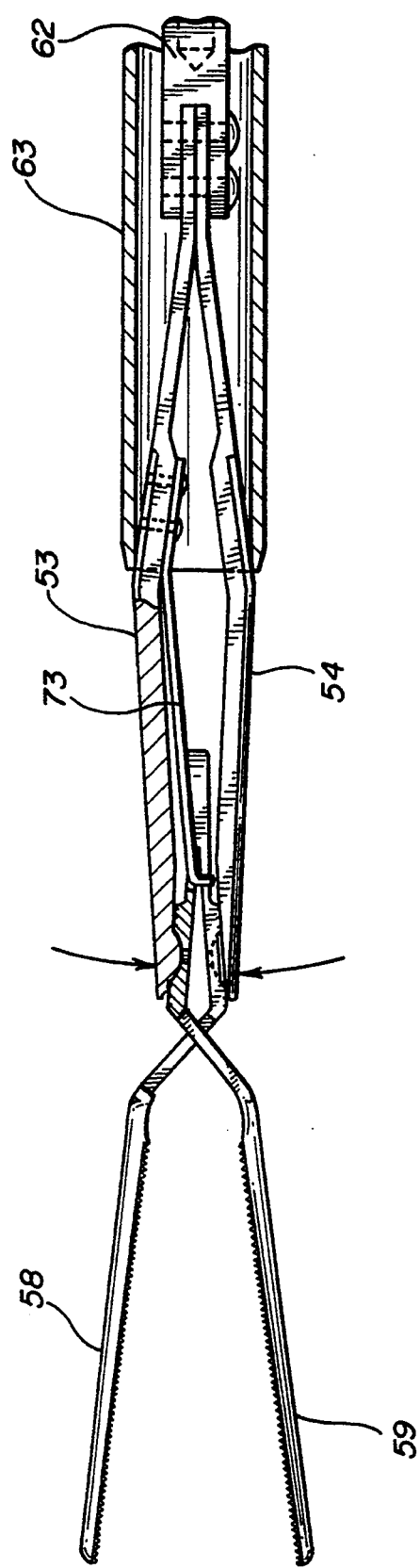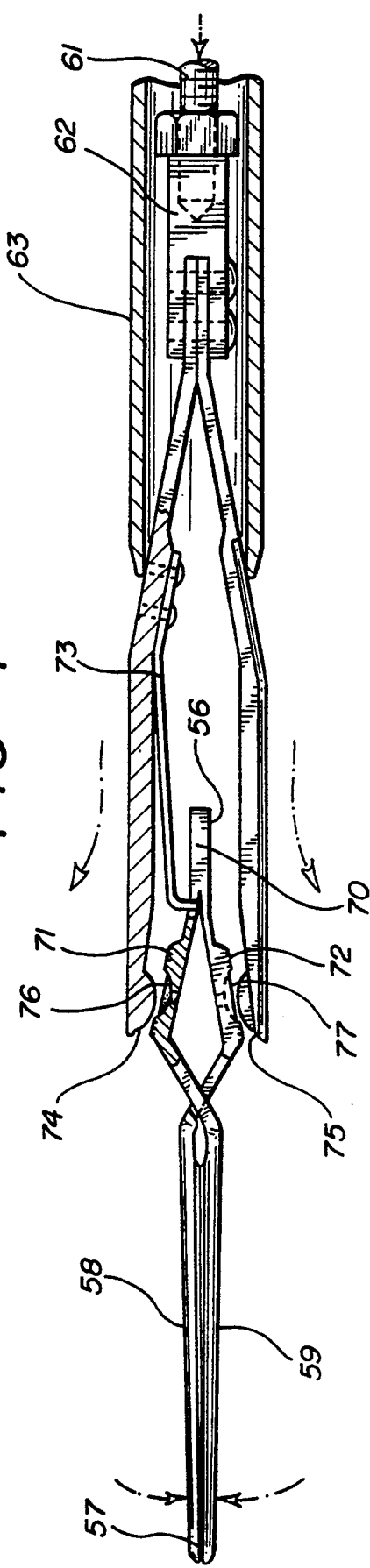

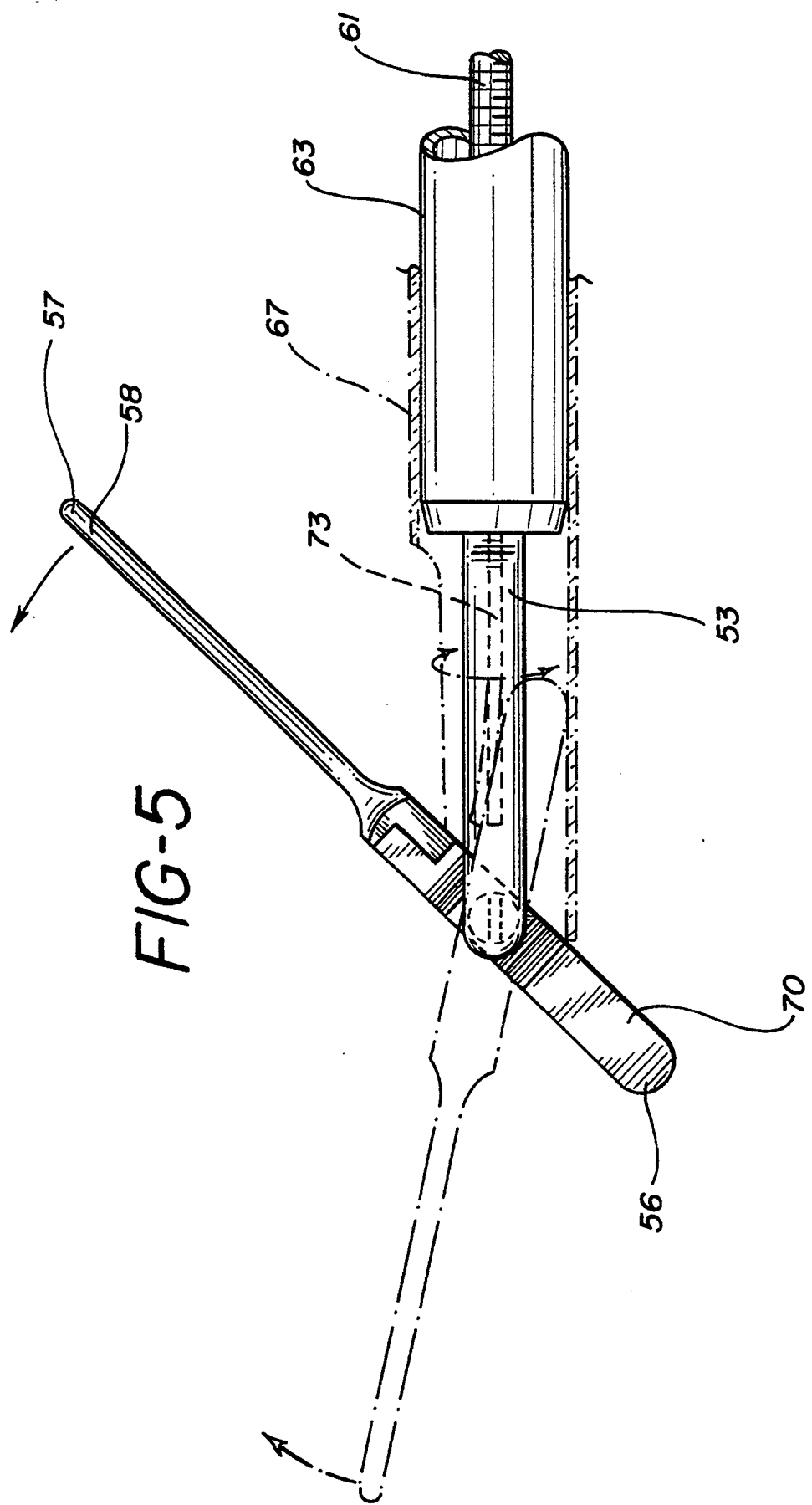

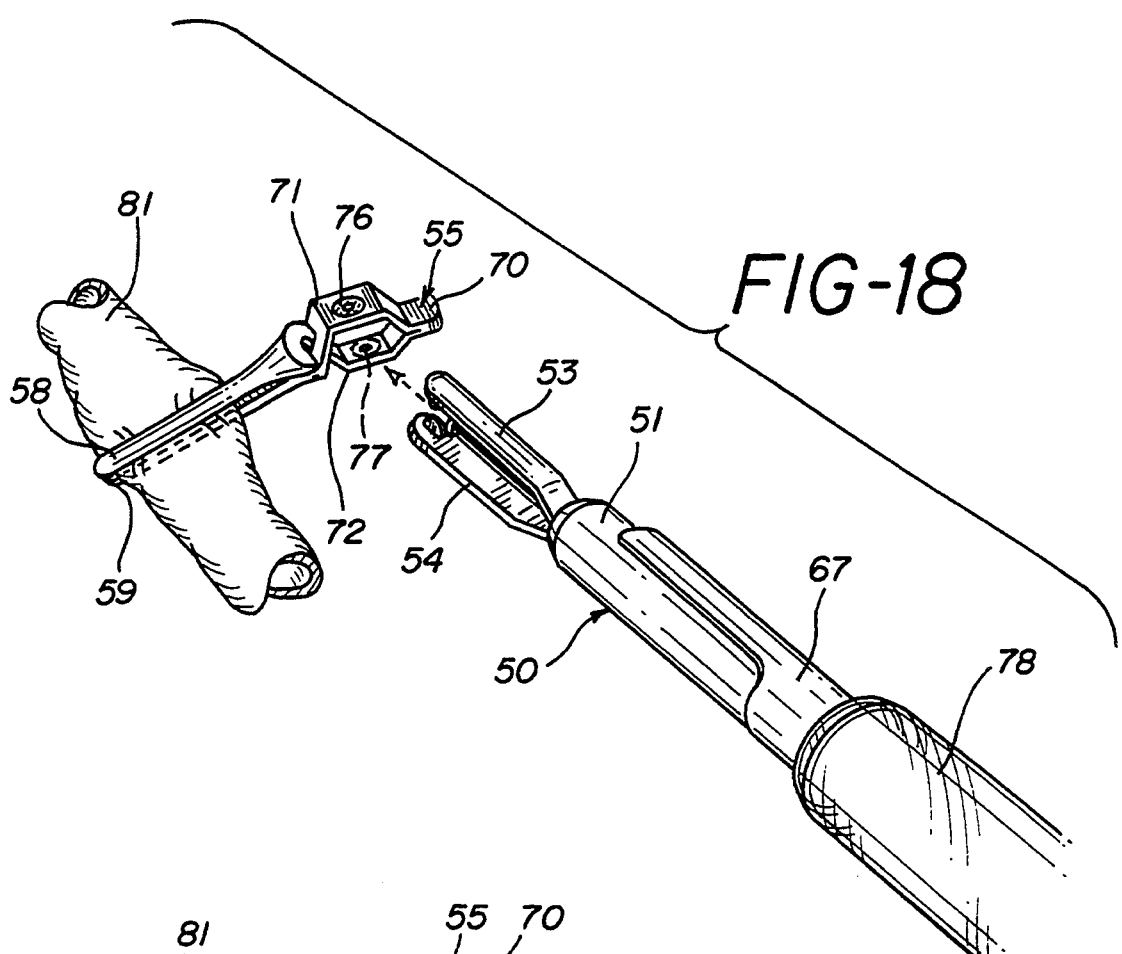
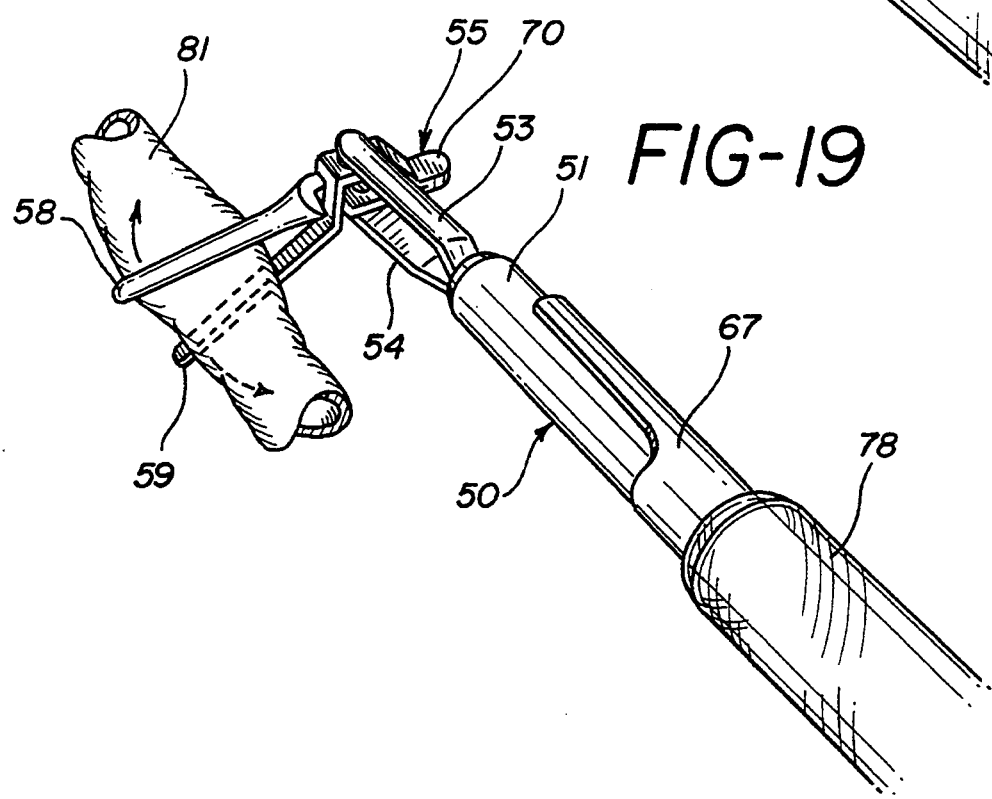

STEERABLE BULLDOG CLAMP APPLIER

BACKGROUND OF THE INVENTION

This invention relates to an instrument for applying a surgical clamp to an internal anatomical structure, usually but not limited to tubular structures more generally referred to as lumens. More specifically, it relates to an endoscopic applier for applying and retrieving a commonly known clamp, conventionally referred to as a "bulldog clamp".

Bulldog clamps are surgical clamps for temporarily occluding numerous kinds of bodily vessels and tubular organs, for example, blood vessels, bowel, ducts, urethra, and the like. These clamps can also be used for clamping other anatomical structure such as the lung, liver or adnexa, where it is often necessary to clamp not only for occlusion, but also for retraction. The occlusion of these anatomical structures, especially tubular structures, is often necessary during surgery to prevent leakage of lumen contents at the surgical site.

One of the chief characteristics of bulldog clamps is that they are designed for temporary clamping only. In other words, the clamp is intended to clamp a structure, e.g. occlude a vessel or tubular organ, while the surgery is being performed, and then it is subsequently removed from the occluded vessel or organ when the surgery is completed. Bulldog clamps have been known for years. See, for example, the Codman & Shurtleff Product Catalogue of 1990, which illustrates a variety of bulldog clamps for cardiovascular and thoracic surgical applications. Other examples of these clamps abound. Vascu-Statt ® disposable bulldog clamps are described in a catalogue published by Scanlan International in 1991. Bulldog clamps come in a variety of sizes and configurations, and the clamping force can vary with the clamp design as well.

In order to facilitate the ability to drop off the bulldog clamp after it is clamped about the vessel or tubular organ, and to thereafter grasp and remove the clamp from the vessel or organ following the surgical procedure, the clamp must possess some kind of configuration in addition to its clamping jaws. Typically, the clamp includes a spring loaded handle mechanism for grasping the clamp and for providing the opposing jaw clamping force. More specifically, it has a self-contained spring element in its handle for providing the constricting force to the desired vessel or tubular organ.

While the current conventional design for bulldog clamps has worked well for surgeons in open surgery, modifications to the existing clamps have been necessary for their adaptation to endoscopic surgery. Endoscopic surgery is surgery performed through small ports or openings in the body with the aid of special equipment and surgical instrumentation to allow the surgeon to perform the surgery while observing his operative technique on a video monitor. The small openings are typically made using a trocar, which is a puncturing instrument for providing access through the body wall to the surgical site.

In open surgery, ratcheting scissor-handled type clamps have often been used rather than bulldog clamps. These scissor-handled clamps use the surgeon's hand force and a ratchet mechanism to apply and retain the clamping force. However, such clamps cannot fit conveniently down trocars. Therefore, with the advent of endoscopic surgery, ratcheting ring-handled clamps, especially designed for endoscopic use, were developed. Unfortunately, these clamps require full-time dedicated trocar ports, thus limiting the number of other instruments which the surgeon can introduce at any one time when the number of trocar ports remain constant.

Since drop-off bulldog clamps provide a tremendous advantage over conventional, scissor-handled clamps during endosurgery, a challenge has been how to introduce these clamps into the body, clamp them onto the desired anatomical structures and in the desired orientation, free the access port for other uses, and then retrieve them through a port when their function is fulfilled. Therefore, it has become necessary to develop a suitable endoscopic applier to apply such drop-off bulldog clamps.

Fortunately, design engineers have begun to rise to the challenge of designing an endoscopic applier to apply and subsequently remove bulldog clamps endoscopically. These applier designs have also taken into consideration some of the modifications needed to the clamp itself for proper functioning with the applier. A good example of such an applier/clamp combination is described in a catalogue published by Birtcher/SOLOS in 1992, which illustrates an applier for the G.I.-1085 Bowel Bulldog Clamp with 40 mm jaw. This applier can be removed from the surgical access port after the clamp has been applied to a vessel. The applier has a palm-actuated handle which causes a camming tube located inside a longitudinal shaft to move distally. The camming tube urges a pivoting jaw toward an opposed fixed jaw. A pair of cylindrical pins are displayed on the inner surfaces of the jaws for securing the clamp. The clamp has a hole through its grip or handle portion for receiving the cylindrical pins (unlike conventional clamps used for open surgery which do not have such a hole). When the jaws of the applier are closed, the jaws of the clamp are correspondingly biased open for clamping about a vessel. The shaft of the applier can rotate, and the clamp can pivot about the cylindrical pins of the jaws to provide variable positioning of the clamp at the surgical site.

A similar device is described in U.S. Pat. No. 4,706,668. This patent discloses an aneurysm clip plier. The plier has a hollow barrel terminating at its distal end with a Y-shaped clip grip. This grip has two opposed arms, and each arm has a projection for engaging corresponding dimples in the clip. The opposed arms of the Y-shaped grip are forced towards each other to open the clip for application to a vessel when a pusher bar is forced against the grip. The pusher bar is activated when a trigger on the handle of the plier is squeezed.

While the art has illustrated certain advances in the design of bulldog clamps and applier mechanisms for using such clamps during endoscopic surgical procedures, a significant drawback with these appliers still exists. Although the appliers which have been described provide the ability to rotate the clamp about the axis of the shaft of the applier, and to allow pivoting of the clamp within the jaws of the applier, the surgeon is unable to pivot the clamp within the jaws of the applier without using another instrument, or alternatively, without pushing the clamp against adjacent bodily anatomy. Obviously, this can present a tremendous inconvenience for the surgeon, who would much prefer having the ability to "steer" the clamp on the applier without these restraints.

The ability of the surgeon to pivot the bulldog clamp on the applier during use should not be underestimated. It is often critical during surgery to precisely position the clamp on the tubular organ, vessel, or any other structure desired to be occluded or clamped. This requires the corresponding ability of the surgeon to properly angulate the clamp when the applier is placed through the small access opening or port during endoscopic surgery. Likewise, it is necessary following removal of the clamp from the vessel or organ to have the ability to align the clamp with the axis of the longitudinal shaft of the applier to facilitate its removal from the body cavity.

One attempt to address the need for pivoting action of a surgical article within the jaws of an endoscopic applier is the development of "articulating" appliers. An articulating applier is an applier whose distal end is capable of articulating from the longitudinal axis of the shaft of the applier up to or even more than 90°, similar to the manner in which a knee joint articulates. While this may address needed problems in many instances, the length of that portion of the shaft of the applier distal to the articulating joint must have a minimum length for clearance within the limited volume of space available in endosurgical procedures.

In view of the deficiencies in the designs for appliers for bulldog clamps, what is needed is an endoscopic applier for a bulldog clamp, which not only can readily place and remove the clamp during endoscopic surgery, but also allows the surgeon to pivot the clamp within the jaws of the applier without altering the direction of any portion of the longitudinal shaft of the applier, More importantly, it would be most beneficial if the ability to "steer" the bulldog clamp could be accomplished without requiring the use of another instrument or the need to push the clamp against adjacent bodily tissue for the desired movement.

SUMMARY OF THE INVENTION

In its broadest aspect, the invention is an endoscopic applier for a surgical clamp. The applier comprises an elongated rod which has first and second arms attached to its distal end. The arms are configured to securely grip the surgical clamp. The applier has means for opening and at least partially closing the arms from the proximal end of the rod. In addition, the applier has means for pivoting the surgical clamp gripped within the arms from the proximal end of the rod.

In another aspect, the invention is the combination of a bulldog clamp and endoscopic applier for the clamp. The clamp comprises first and second opposed clamping jaws. The jaws are connected to a handle region for opening and closing the clamping jaws, and the handle region is configured to be accepted by the arms of the endoscopic applier. The applier for this clamp comprises an elongated rod with first and second opposed gripping arms attached to the distal end of the rod. The arms are configured to cooperate with the handle region of the clamp to securely grip the clamp. The applier has means for opening and at least partially closing the arms from the proximal end of the rod. The applier also has means for pivoting the clamp gripped within the arms from the proximal end of the rod.

In yet a further aspect of the invention, this invention is the combination of the bulldog clamp and endoscopic applier, in which the clamp displays clamping jaws at its distal end for clamping an anatomical structure, a common hinge region displayed at its proximal end, and first and second opposed squeezing surfaces connecting the jaws to the common hinge region. The jaws of the clamp are biased closed in their normal rest positions, and may be opened when the squeezing surfaces of the clamp are urged toward each other. The squeezing surfaces are configured to be accepted by the arms of the applier.

The applier for the clamp described in the preceding paragraph comprises an elongated rod having first and second opposed gripping arms attached to the distal end of the rod. The first and second opposed gripping arms are configured to cooperate with and grip the first and second opposed squeezing surfaces of the clamp. The applier also includes a camming barrel enclosing at least a portion of the rod and a portion of the arms so that the arms are partially closed for securely gripping the clamp. The applier has a palm grip attached to the camming barrel and a pivoting trigger attached to the rod. In addition, the applier has means for sliding the rod distally relative to the camming barrel when the trigger is squeezed toward the palm grip, which causes the arms to correspondingly slide outward from the camming barrel to an open position for dropping off or picking up the clamp. Finally, the applier includes means for pivoting the clamp about the opposed squeezing surfaces from the proximal end of the rod when the opposed gripping arms are gripping the clamp.

The clamp and the applier of this invention are especially adapted for use during endoscopic surgery when it becomes necessary to manipulate the applier and clamp through a small access opening to reach the surgical site. The surgeon using the applier can grip the clamp endoscopically, and drop off the clamp at the surgical site without inconvenience or difficulty. In addition, the applier makes it possible to engage the clamp, release it from the tissue and remove the clamp endoscopically once its clamping function is completed.

Most importantly, the applier of this invention is capable of steering the clamp within the arms of the applier from the proximal end of the elongated rod of the applier without requiring the use of a wholly separate instrument or the need to push the clamp against delicate adjacent bodily tissue for the desired pivoting action. In addition, the steering action is possible without requiring the distal end of the elongated rod to articulate from its intended longitudinal axis, thus making it unnecessary to undesirably increase the length of the applier in the angular direction in which the clamp is positioned.

In one embodiment, the pivoting means includes a biasing member mounted on the applier, preferably on the first or second arm of the applier, for biasing the clamp away from the longitudinal axis of the applier rod. This biasing member can be a cantilevered spring, for example, although any other structural member can be used as well. Alternatively, the configuration of the gripping arms of the applier and the complementary handle surfaces of the clamp where the arms grip the clamp can be modified to create a biasing action to bias the clamp away from the longitudinal axis of the elongated rod, in this manner, it then becomes unnecessary to incorporate a structural biasing member on the arms of the applier.

In an especially preferred embodiment, the pivoting means further includes a steering tube slidable over the distal end of the applier for pivoting the intentionally misaligned clamp gripped within the applier arms when the distal end of the steering tube is pushed against the clamp. In addition, the steering tube may also serve the dual purpose of facilitating the insertion of the applier and/or clamp through a trocar port endoscopically. A groove is desirably displayed at the distal end of the steering tube, which allows the surgeon to manipulate the steering tube to engage the clamp for realigning the clamp with the longitudinal axis of the rod for subsequent passage of the clamp into the steering tube.

The applier of this invention can be used to apply any bulldog clamp endoscopically, especially when it is desired to have the ability to "steer" the clamp within the arms of the applier during use. The applier is especially adapted for applying a bulldog clamp modified to be accepted within the arms of the applier. This applier in combination with the bulldog clamp can be readily used in almost all endoscopic applications requiring clamping of structures including the total or partial occlusion of vessels or tubular organs.

BRIEF DESCRIPTION OF THE DRAWINGS

FIG. 1 is a perspective view of the preferred endoscopic bulldog clamp applier gripping a bulldog clamp.

FIG. 2 is a side elevational view in partial cross-section of the applier and clamp of FIG. 1 with the steering tube of the applier detached from the instrument.

FIG. 3 is an enlarged side elevational view shown in partial cross-section of the distal end of the applier with the bulldog clamp shown in an open first position.

FIG. 4 is an enlarged side elevational view shown in partial cross-section of the distal end of the applier with the bulldog clamp shown in a closed second position.

FIG. 5 is an enlarged top plan view of the distal end of the applier.

FIGS. 11 through 21 are views illustrating the procedural movements required to enable placement and removal of the bulldog clamp with the applier endoscopically.

DETAILED DESCRIPTION OF THE PREFERRED EMBODIMENTS

Figure 6:
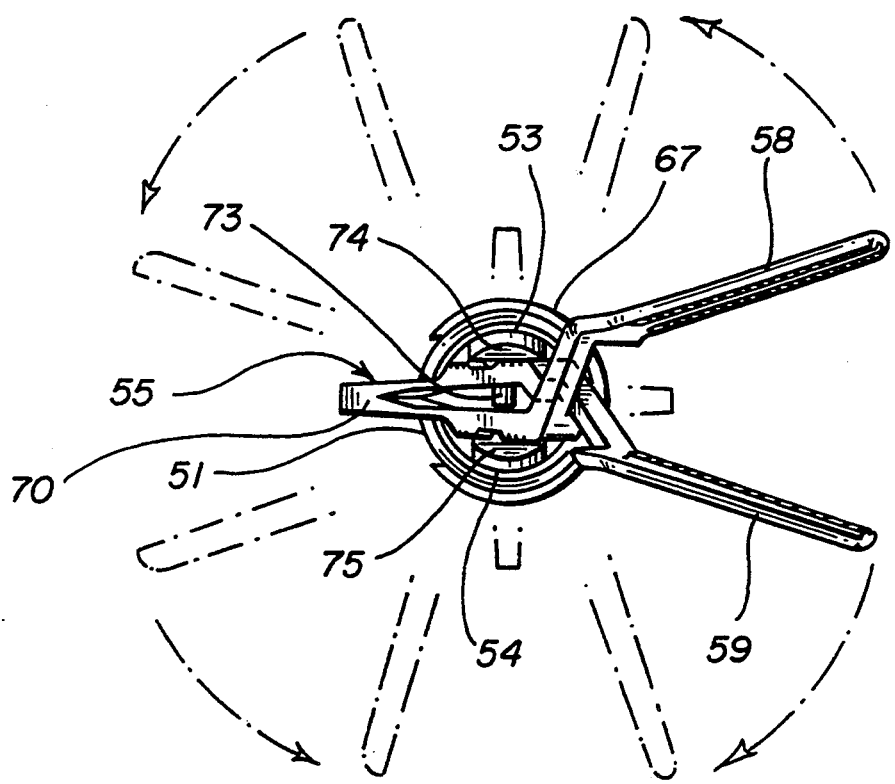
FIG. 6 is an enlarged distal end view of the applier and bulldog clamp.
Figure 7:
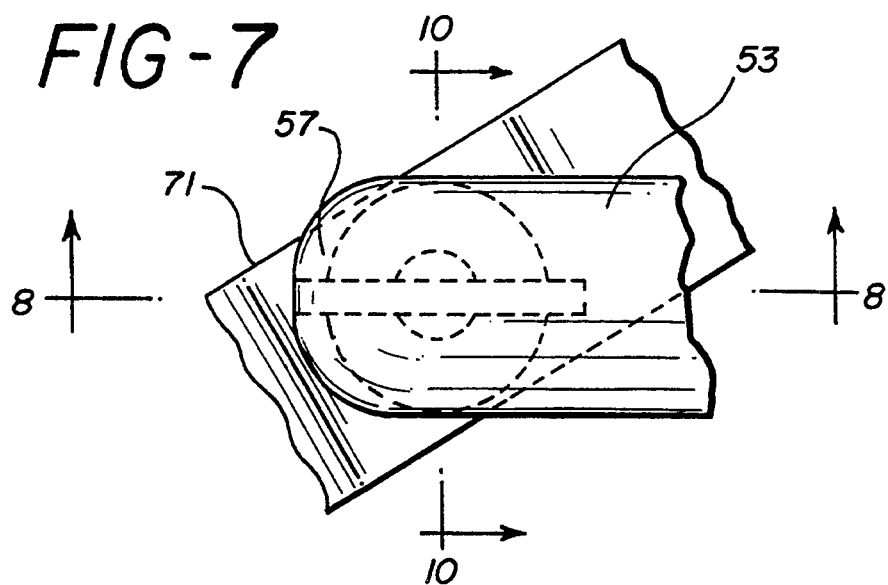
FIG. 7 is an enlarged top plan view of the gripping portion of the arms of the applier and a portion of the bulldog clamp.
Figure 8:
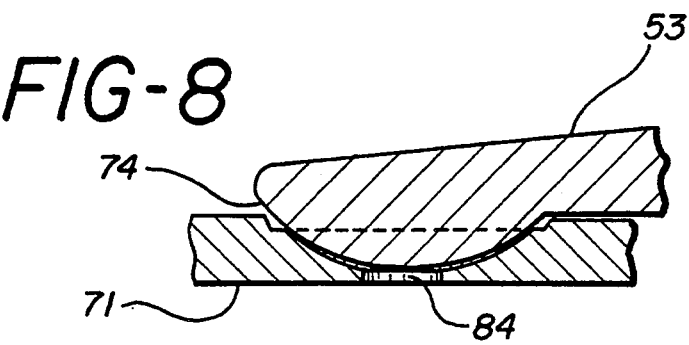
FIG. 8 is a cross-sectional view as taken along line 8—8 of FIG. 7.
Figure 9:
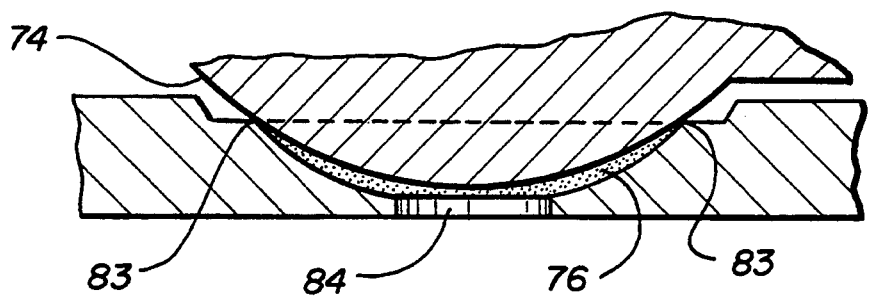
FIG. 9 is an enlarged portion of FIG. 8 showing the point of contact between the gripping portion of the arms of the applier and the bulldog clamp.
Figure 10:
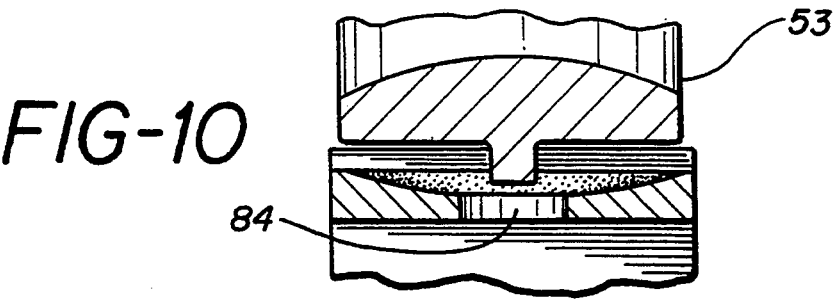
FIG. 10 is a cross-sectional view as taken along line 10—10 of FIG. 7.
Figure 11:
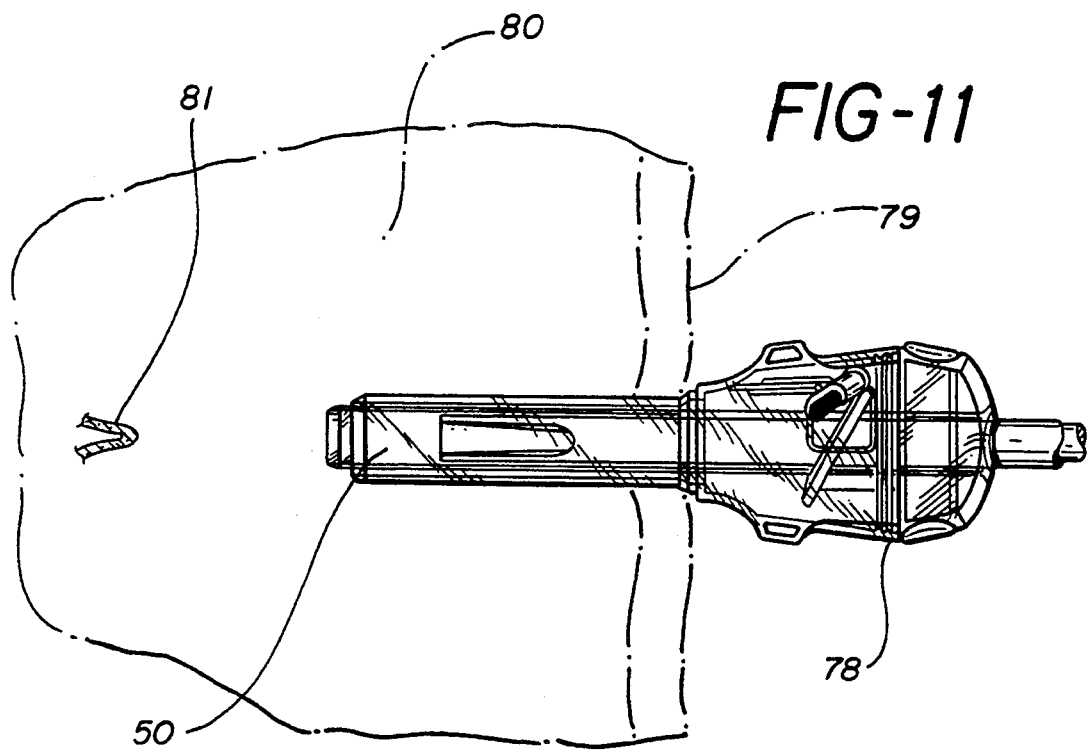
Figure 12:
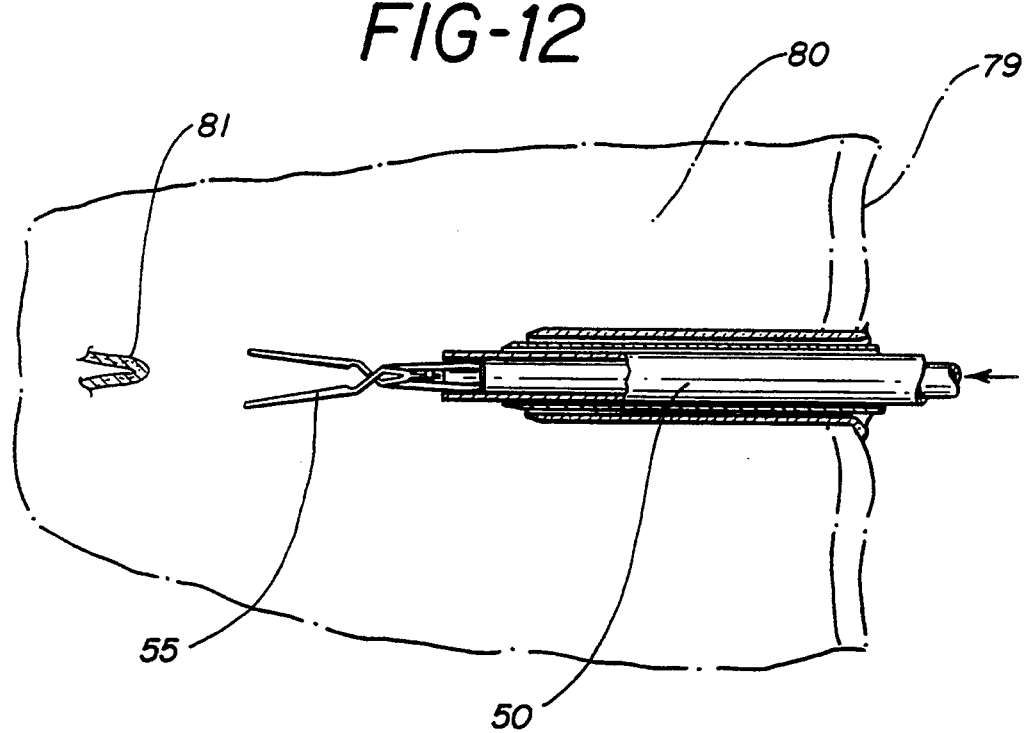
Figure 13:
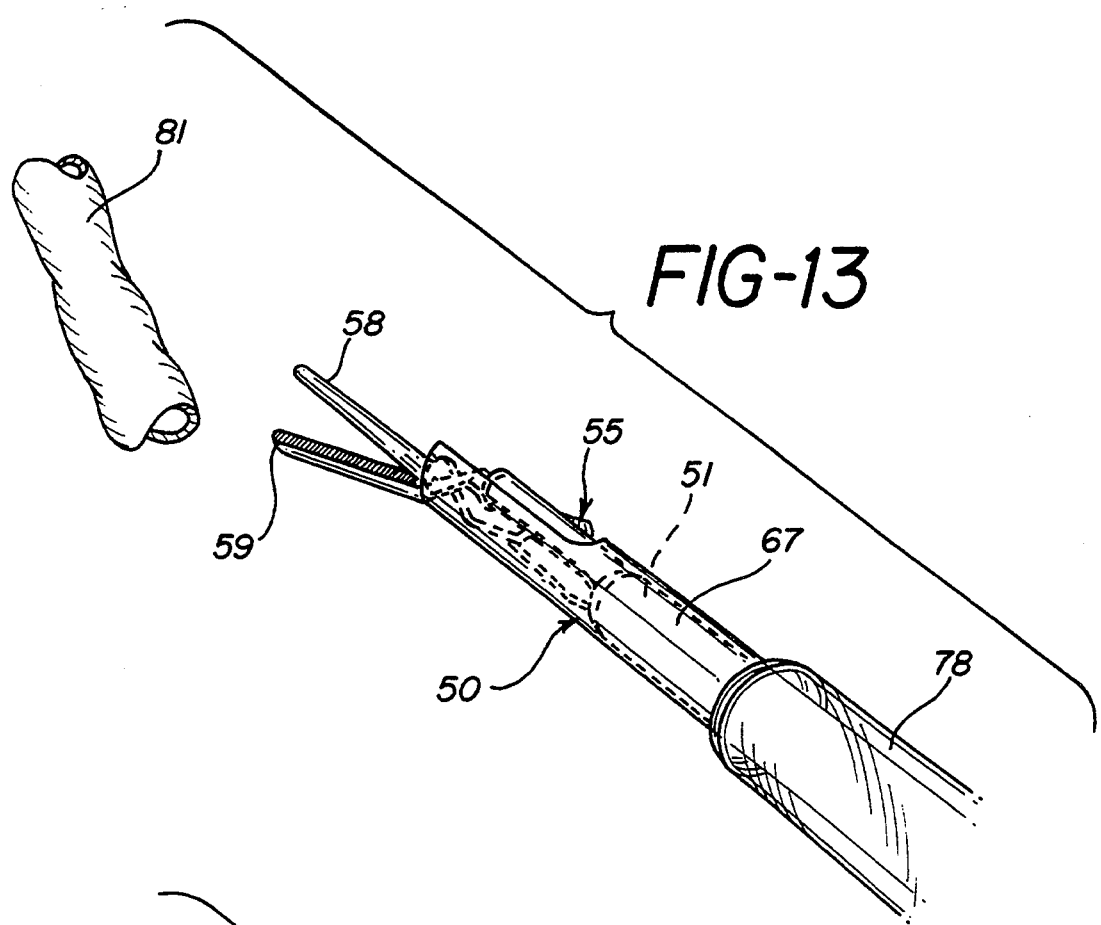
Figure 14:
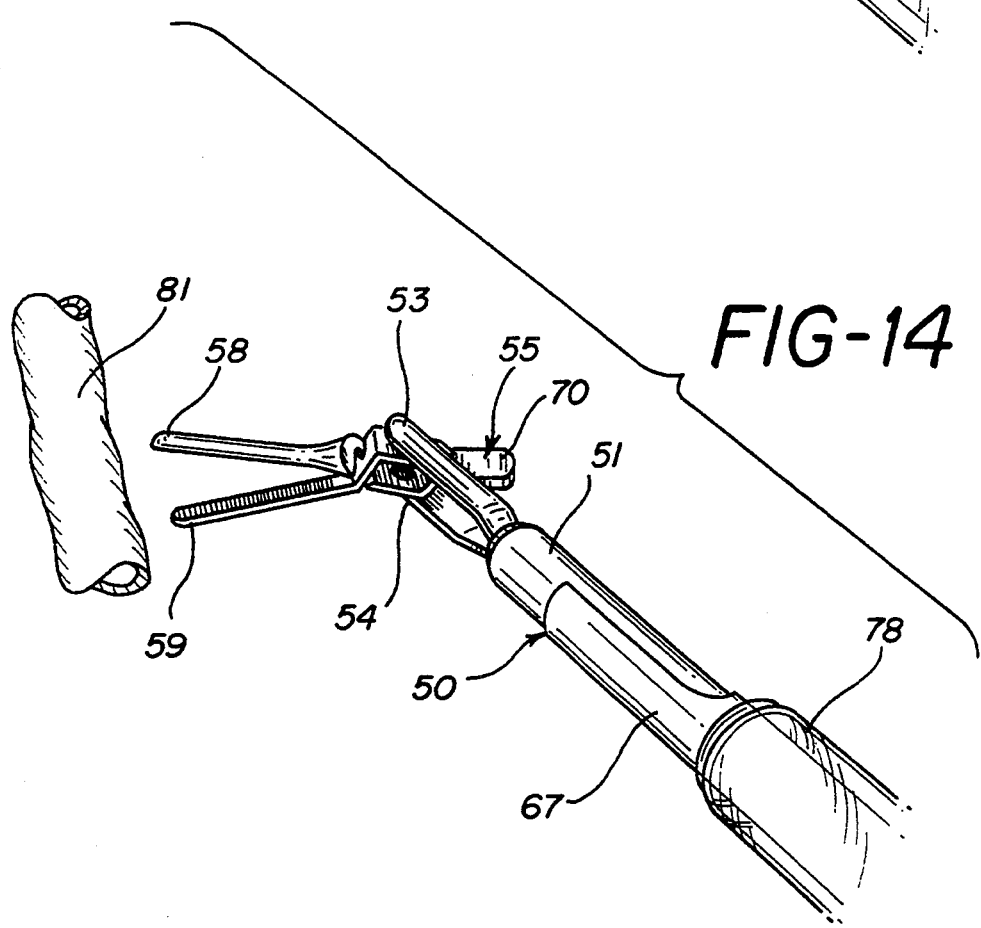
Figure 15:
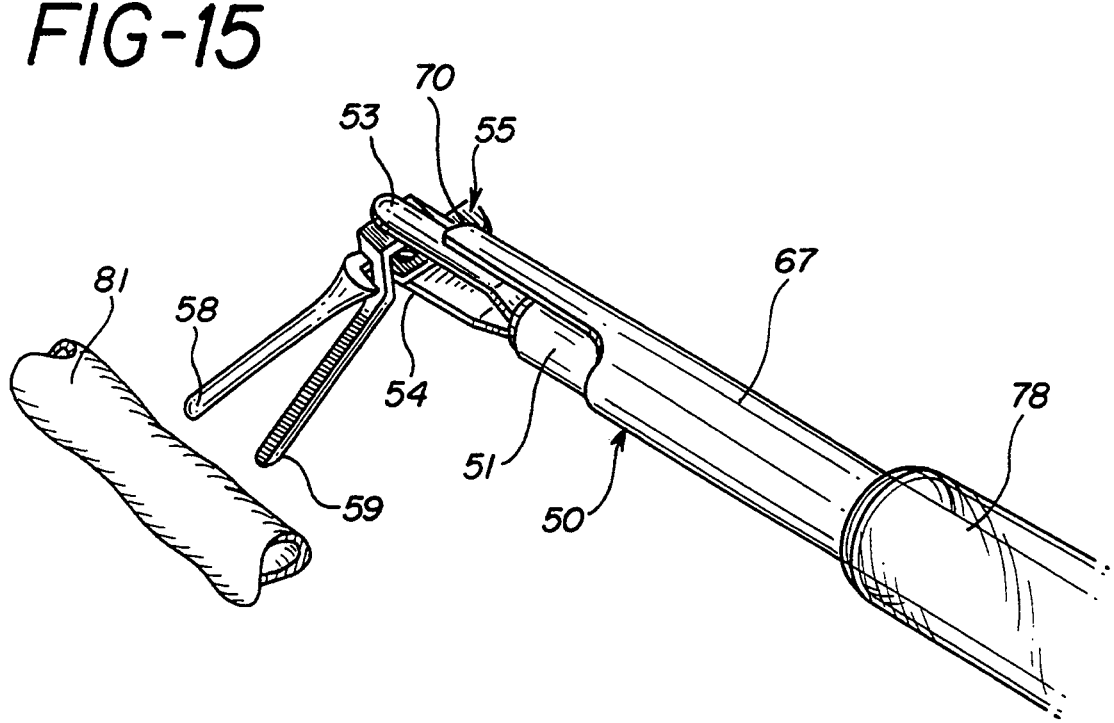
Figure 16:
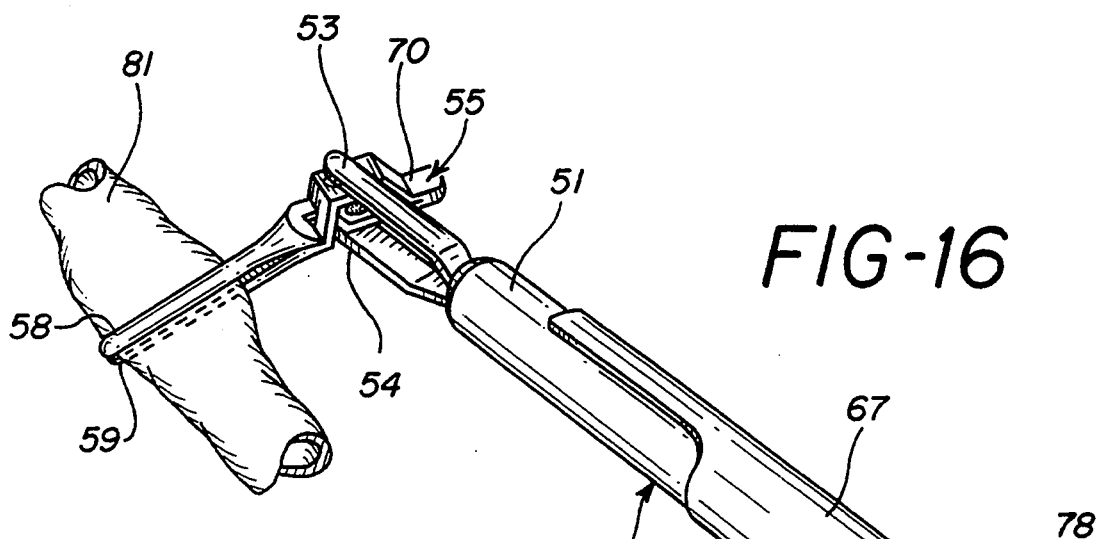
Figure 17:
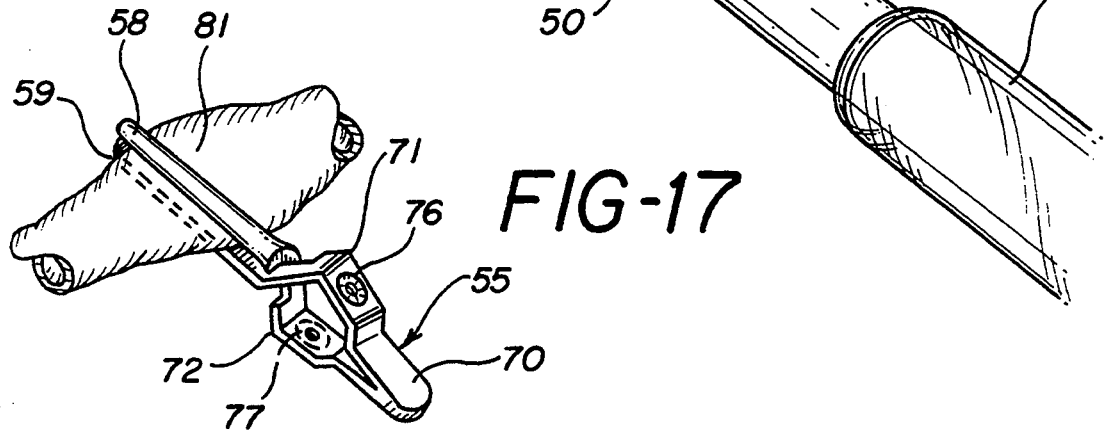
Figure 20:
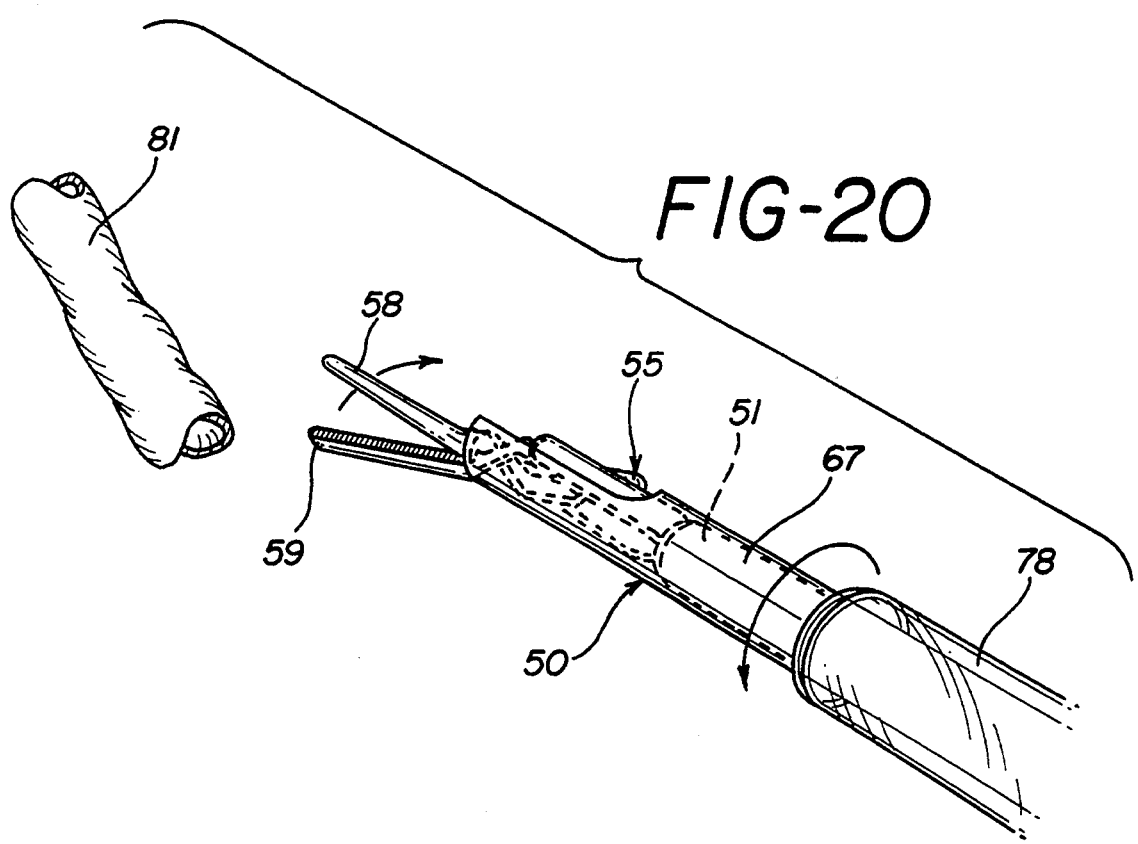
Figure 21:
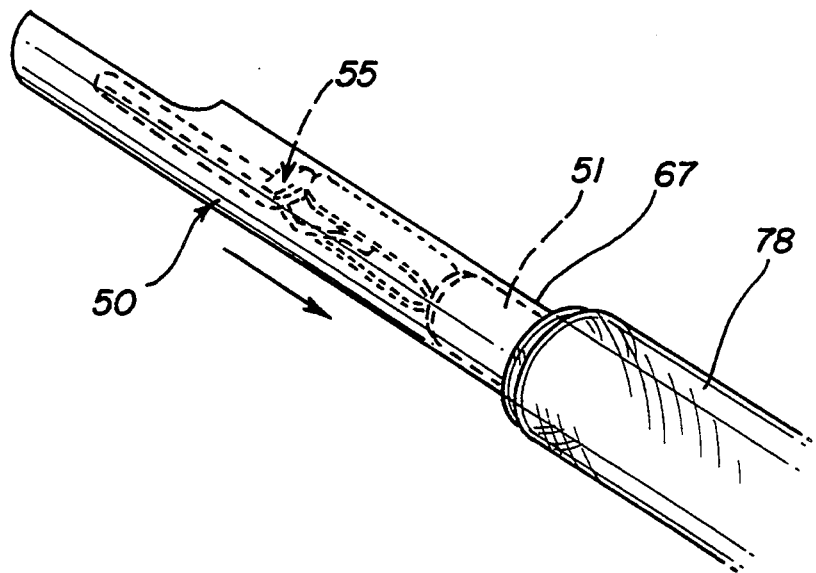

For the purpose of describing this invention, a bulldog clamp is any surgical clamp used for temporarily clamping an anatomical structure, often for the occlusion of a bodily vessel or tubular organ. Optimally, it is configured to allow the surgeon the ability to first manipulate the clamp into place relative to the structure, apply the clamp, detach the clamp from the applier, and then retrieve and remove the clamp from the surgical site at a later desired time. In this way, the trocar cannula which provides the port for inserting the clamp can be freed for insertion of other instruments until it becomes necessary for the surgeon to remove the clamp.

The term "distal" refers to that portion of the applier or clamp extending away from the user, and the term "proximal" refers to that portion of the applier or clamp extending toward the user. Similarly, "distally" and "proximally" refer to movement extending away from the user during use and toward the user during use, respectively.

Referring now to the Figures, and FIG. 1 specifically, there is shown a bulldog clamp applier 50 for applying and removing a bulldog clamp 55 during an endoscopic surgical procedure where it is desired to temporarily clamp an anatomical structure. The applier 50 has an endoscopic portion 51 configured to fit through a small diameter opening, or trocar cannula, during the surgical procedure. Attached to the proximal end of the endoscopic portion 51 of the applier is the handle portion 52. The handle portion 52 allows the surgeon to activate the mechanisms in the endoscopic portion 51 to grip and detach a bulldog clamp from the distal end of the applier. The clamp is gripped and detached with the aid of the first and second resiliently opposed gripping arms 53, 54, respectively.

The bulldog clamp 55 for temporarily occluding the desired anatomical structure has proximal and distal ends 56, 57, respectively, and first and second opposed clamping jaws 58, 59, respectively, for clamping about the anatomical structure. The clamping jaws are biased closed in their normal rest position, and are opened for clamping about the desired anatomical structure when the clamp is gripped within the opposed gripping arms 53, 54 of applier 50. The applier 50 has a rotation knob 60 for providing rotational movement of the opposed gripping arms 53, 54, and consequently rotational movement of the bulldog clamp 55.

Referring specifically now to FIG. 2, it can be seen that the endoscopic portion 51 of applier 50 has an elongated threaded rod 61. This threaded rod is attached to a jaw connecting means 62 at the distal end of the rod. The jaw connecting means 62 provides a mounting structure for the resiliently opposed gripping arms 53, 54 of the applier. The proximal end of the threaded rod 61 is attached to the rotation knob 60, so that when the rotation knob is rotated, it in turn rotates the threaded rod and jaw connecting means 62, which consequently turns the opposed gripping arms 53, 54 as well. A camming barrel 63 encloses the threaded rod 61 and a portion of the opposed gripping arms 53, 54.

The handle portion 52 of the applier 50 has a palm grip 64 and a pivoting trigger 65 for providing the surgeon with the requisite capability to open and close the opposed gripping arms 53, 54. The palm grip 64 is attached to the camming barrel 63, and the pivoting trigger 65 is attached to the threaded rod 61. When the surgeon squeezes the pivoting trigger 65, the threaded rod 61 moves distally, which correspondingly causes the opposed gripping arms 53, 54 to move distally. As the opposed arms move distally, the arms slide outward from the camming barrel 63. When the arms are displayed in this outward position, the arms are open to accept a bulldog clamp. When the surgeon releases the trigger 65, the threaded rod and attached gripping arms move proximally, and a portion of the gripping arms 53, 54 are subsequently constrained within the camming barrel 63 to maintain the arms in a partially closed position for gripping the bulldog clamp. The threaded rod 61 is maintained in the rearward, proximal position by spring 66.

A steering tube 67 fits over the camming barrel 63 of the applier 50. The steering tube is sized to provide easy rotational movement of the steering tube about the camming barrel, as well as sliding movement of the steering tube proximally and distally along the barrel. The steering tube should have tube a length which allows the surgeon to slide the steering tube distally over the opposed clamping jaws of the bulldog clamp 55, while still retaining the ability to perform this sliding movement from a position outside of the body cavity during endoscopic surgery. The steering tube 67 has a spindle 68 to facilitate rotational and sliding movement by the surgeon, and a groove 69 to permit the pivoting and placement of the clamp in a direction parallel to the longitudinal axis of the applier for insertion endoscopically through a trocar cannula, which is illustrated and explained in further detail with respect to FIGS. 11 to 21.

FIGS. 3 and 4 provide a detailed view of the cooperative elements enabling the gripping of the bulldog clamp in the arms of the applier. The bulldog clamp has a common sprung hinge region 70 at its proximal end. First and second opposed squeezing surfaces 71, 72, respectively, of the clamp connect the common hinge region 70 with the opposed clamping jaws 58, 59. The gripping arms 53, 54 have corresponding first and second opposed projections 74, 75 respectively, at their distal ends to facilitate gripping of the bulldog clamp. The squeezing surfaces 71, 72 of the clamp likewise display corresponding first and second socket-like indentations 76, 77 respectively. The opposed projections 74, 75 of the gripping arms mate with their corresponding opposed indentations 76, 77 of the squeezing surfaces of the clamp to provide a firm and secure grip of the clamp at the distal end of the arms of the applier. When the arms of the applier grip the clamp, the opposed projections 74, 75 urge the opposed squeezing surfaces 71, 72 at the indentations 76, 77 together, which in turn causes the opposed clamping jaws 58, 59 of the clamp to open. Similarly, when the grip is released, the squeezing surfaces move apart to their original position, causing the clamping jaws 58, 59 to come into contact with each other. Finally, a cantilevered spring 73 is attached to the first gripping arm 53 to bias the common hinge region 70 of the clamp away from the longitudinal axis of the endoscopic portion of the applier. This is desirable to provide the surgeon with the ability to pivot the clamp when it is gripped within the arms of the applier, as discussed in further detail below.

The degrees of movement of the clamp within the arms of the applier are illustrated in FIGS. 5 and 6. The clamp is pivotable about the distal end of the opposed gripping arms. Additionally, the clamp is capable of rotational movement. This flexibility in pivoting and rotation are critical during endoscopic surgery, to enable the surgeon to precisely position the clamping jaws of the bulldog clamp about the desired anatomical structure.

Referring now to FIGS. 7 to 10, there is shown the relative orientation of the squeezing surface of the clamp in relation to the gripping arm of the applier, and the structural fit between the projection 74 displayed at the distal end of gripping arm 53 and the socket-like indentation 76 of the squeezing surface 71 of the clamp. The cantilevered spring 73, shown in FIGS. 3 and 4, bias the common hinge region of the clamp off center, therefore positioning squeezing surface 71 away from the longitudinal axis of gripping arm 53. Upon a careful review of FIGS. 8 to 10 specifically, it can be seen that the radius of curvature of the projection 74 is slightly greater than the corresponding radius of curvature of indentation 76. This difference in the radii of curvature ensures that the primary contact region between the indentation and projection is near the periphery 83 of the projection. This feature is desirable to provide resistance to unintentional pivoting. Alternatively, additional methods can be used to achieve this increased resistance. For example, contact near the periphery is also achieved when the indentations have an opening 84 through them. Alternatively, or in combination with opening 84, the surface of the indentations or projections can be roughened to achieve further increased resistance.

Referring now to FIGS. 11 to 21 in combination, the technique for applying and removing the bulldog clamp and applier through a trocar endoscopically, while achieving precise pivoting movement of the clamp at the site of the anatomical structure desired to be clamped, is illustrated. At the beginning of the procedure, the clamp is first placed in the arms of the applier, and the steering tube is fully advanced over the entire clamp. The applier and clamp are then capable of being inserted through trocar 78. The steering tube is moved proximally to allow the bulldog clamp 55 to protrude from the distal end of the applier 50 (see FIG. 12). When the steering tube is no longer enveloping the clamp 55, the clamp pivots to an acute angle because of the biasing action of the cantilevered spring 73 (see FIGS. 3 and 4). When the surgeon positions the clamp 55 near the desired anatomical structure 81 to be clamped, the surgeon is then ready to pivot the clamp to a precise position to facilitate the clamping of the anatomical structure. The surgeon accomplishes this positioning by advancing the steering tube 67 so that it contacts the common hinge region of the clamp. By continuing to advance the tube, the angle of the clamp relative to the applier continues to increase. In this manner, the surgeon is able to pivot the clamp to the desired position. Once the desired angular orientation of the clamp is achieved, the surgeon can stop advancing the steering tube, and instead retract the steering tube proximally so that the clamp can be placed over the desired anatomical structure 81. When the clamp is placed over the structure, the surgeon can then release the applier and withdraw it from the trocar, leaving the bulldog clamp securely clamped about the anatomical structure (see FIG. 17).

When the surgeon desires to remove the clamp from the anatomical structure 81, the surgeon reinserts the applier through the trocar, then slides the steering tube proximally and positions the applier near the clamp. The surgeon opens the arms of the applier by squeezing the trigger toward the palm grip on the handle portion of the applier. He/she positions the projections on the distal ends of the arms of the applier over the socket-like indentations of the squeezing surfaces of the clamp, and then releases the trigger on the applier to close the projections on the gripping arms within the indentations displayed on the squeezing surfaces of the clamp. The anatomical structure is thus released from the clamping jaws of the clamp, and the clamp can then be withdrawn from the structure. At this point, the surgeon advances the steering tube distally towards the clamp. The surgeon then positions the steering tube so that the steering tube is pushed against the clamp at a point distal from the common hinge region. This ability to push the clamp at a position distal to the common hinge region is made possible because of the inclusion of the groove 69 displayed at the distal end of the steering tube (see FIG. 2). In this manner, the clamp is realigned with the longitudinal axis of the applier as the surgeon continues to advance the steering tube. Once the steering tube is fully extended over the distal end of the jaws of the bulldog clamp, a proper alignment of the clamp with the longitudinal axis of the applier is achieved, and the applier and clamp can then be subsequently withdrawn from the trocar.

Figure 22:
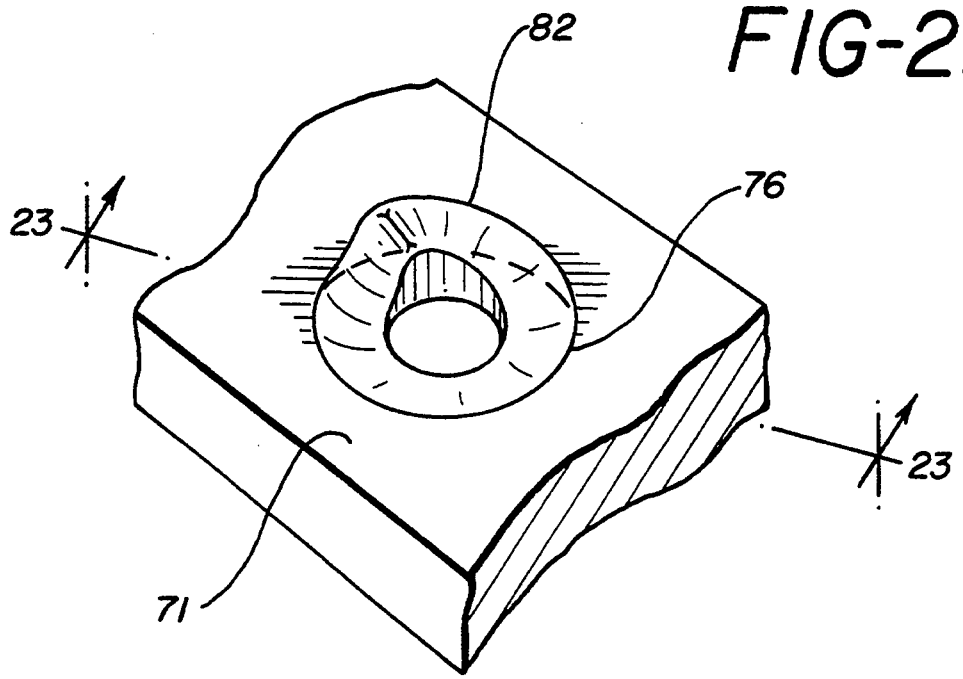
FIGS. 22 and 23 are a perspective view and a cross-sectional view, respectively, disclosing an alternative means to bias the bulldog clamp off center.
Figure 23:
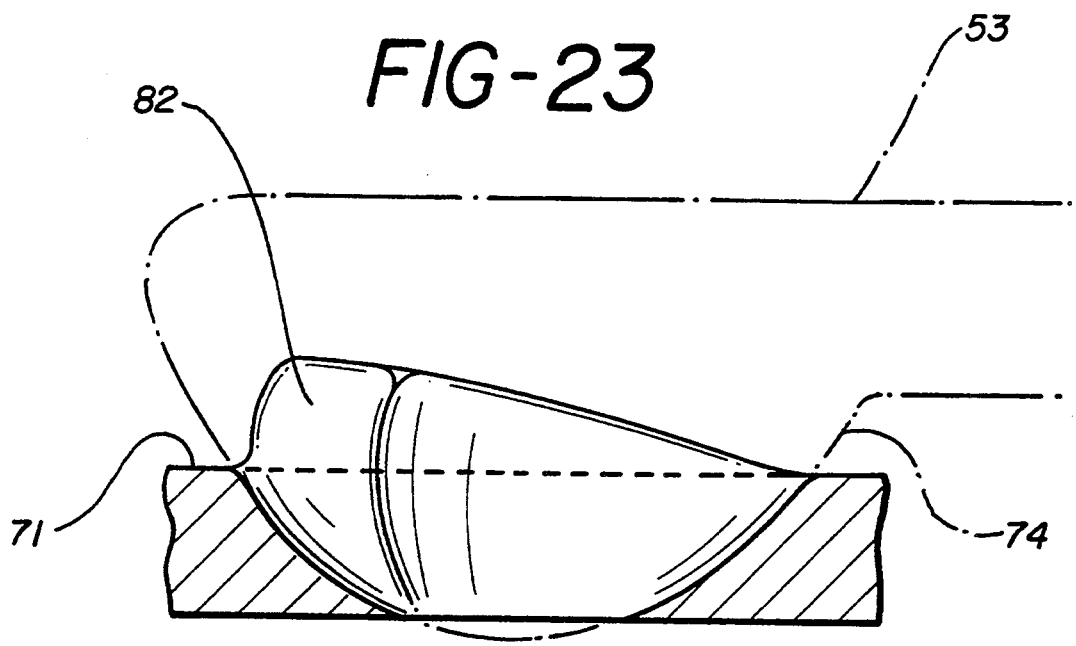

In another embodiment of this invention, an alternative means is used to bias the common hinge region of the clamp off center from the longitudinal axis of the applier. FIGS. 22 and 23 illustrate a means for biasing which represents an alternative to the cantilevered spring 73 shown specifically in FIGS. 3 and 4. As shown in FIGS. 22 and 23, the socket-like indentation 76 of the squeezing surface 71 of the clamp displays a sloping ridged region 82 which provides a sloping region about the periphery of the indentation 76. The sloping ridged region is desirably positioned along the longitudinal axis of the clamp so that when the projection 74 at the distal end of gripping arm 53 contacts this sloping ridged region surrounding the periphery of the indentation 76, the squeezing surface 71 of the clamp is urged off center from the longitudinal axis of the gripping arm of the applier.

Although this invention has been described in relation to its preferred embodiments, numerous additional embodiments within the scope and spirit of the invention as set forth in the appended claims are well within the reach of those skilled in the art.

What is claimed is:

1. An endoscopic applier for a surgical clamp, said applier comprising:
   a) an elongated rod;
   b) first and second arms attached to the distal end of said rod, said arms configured to securely grip said surgical clamp;
   c) means for opening and at least partially closing said arms from the proximal end of said rod; and
   d) means for pivoting said clamp in said arms from the proximal end of said rod, said pivoting means including a biasing member mounted on said first or second arm for biasing said surgical clamp away from the longitudinal axis of said rod.

2. The applier of claim 1 wherein said pivoting means further includes a steering tube slidable over the distal end of said applier for pivoting said biased clamp in said arms of said applier when the distal end of said steering tube is pushed against said clamp.

3. The applier of claim 2 wherein said steering tube has a groove displayed at its distal end so as to allow said clamp to realign with the longitudinal axis of said rod in said arms of said applier for passage of said clamp into said steering tube.

4. The applier of claim 1 wherein said biasing member is a cantilevered spring.

5. In combination, a bulldog clamp and an endoscopic applier for said clamp,
   said clamp comprising first and second opposed clamping jaws; and a handle region connected to said jaws for opening and closing said clamping jaws;
   said applier comprising an elongated rod; first and second opposed gripping arms attached to the distal end of said rod, said arms cooperating with said handle region of said clamp to securely grip said clamp; means for opening and at least partially closing said arms from the proximal end of said rod, and means for pivoting said clamp in said arms from the proximal end of said rod said pivoting means including a biasing member mounted on said applier for biasing said handle region of said clamp away from the longitudinal axis of said rod.

6. The clamp/applier combination of claim 5 wherein said pivoting means further includes a steering tube slidable over the distal end of said applier for pivoting said biased clamp in said arms of said applier when the distal end of said steering tube is pushed against said handle region of said clamp.

7. The clamp/applier combination of claim 6 wherein said steering tube has a groove displayed at the distal end of said steering tube so as to allow said handle region of said clamp to realign with the longitudinal axis of said rod in said arms of said applier for passage of said clamp into said steering tube.

8. The clamp/applier combination of claim 5 wherein said biasing member is a cantilevered spring.

9. In combination, a bulldog clamp and an endoscopic applier for said clamp,
   said clamp comprising a proximal and distal end; first and second opposed clamping Jaws displayed at said distal end for clamping an anatomical structure, said opposed clamping jaws being biased closed; a common hinge region displayed at said proximal end; and first and second opposed squeezing surfaces connecting said jaws to said common hinge region for opening said opposed clamping jaws when said squeezing surfaces are urged toward each other, said squeezing surfaces configured to be accepted by the arms of said endoscopic applier;
   said endoscopic applier comprising an elongated rod having a proximal and distal end; first and second opposed gripping arms attached to said distal end, said first and second opposed gripping arms configured to cooperate with and grip said first and second opposed squeezing surfaces of said clamp; a camming barrel enclosing at least a portion of said rod and a portion of said arms so as to partially close said arms for securely gripping said clamp; a handle portion having a palm grip attached to said camming barrel and a pivoting trigger attached to said rod; means for sliding said rod distally relative to said camming barrel when said trigger is squeezed toward said palm grip, thereby causing said arms to correspondingly slide outward from said camming barrel to an open position for engaging or dropping off said clamp; and means for pivoting said clamp about said opposed squeezing surfaces from said proximal end of said rod when said opposed gripping jaws are gripping said clamp, said pivoting means including a biasing member mounted on said first or second arm for biasing said surgical clamp away from the longitudinal axis of said rod.

10. The clamp/applier combination of claim 9 wherein said elongated rod is rotatable.

11. The clamp/applier combination of claim 9 wherein said pivoting means further includes a steering tube slidable over the distal end of said camming barrel for pivoting said biased clamp in said gripping arms of said applier when the distal end of said steering tube is pushed against said common hinge region of said clamp.

12. The clamp/applier combination of claim 11 wherein said steering tube has a groove displayed at the distal end of said steering tube so as to allow said common hinge region to realign with the longitudinal axis of said rod for passage of said clamp into said steering tube when said steering tube is pushed against said clamp at a point distal from said common hinge region.

13. The clamp/applier combination of claim 9 wherein said biasing member is a cantilevered spring.

14. The clamp/applier combination of claim 9 wherein said first and second opposed gripping arms have first and second opposed, generally semi-circular projections for gripping said squeezing surfaces of said clamp.

15. The clamp/applier combination of claim 14 wherein said first and second opposed squeezing surfaces have first and second curved socket-like indentations configured to accept said first and second opposed projections, respectively.

16. The clamp/applier combination of claim 15 wherein the radii of curvature of said indentations are less than the radii of curvature of said projections.

17. The clamp/applier combination of claim 16 wherein said socket-like indentations have a sloping ridged region for biasing said common hinge region of said clamp away from the longitudinal axis of said rod when said projections of said opposed gripping arms engage said indentations.

18. The clamp/applier combination of claim 17 wherein said pivoting means includes a steering tube slidable over the distal end of said camming barrel for pivoting said biased clamp in said gripping arms of said applier when the distal end of said steering tube is pushed against said common hinge region of said clamp.

19. The clamp/applier combination of claim 18 wherein said steering tube has a groove displayed at the distal end of said steering tube so as to allow said common hinge region to realign with the longitudinal axis of said rod for passage of said clamp into said steering tube when the distal end of said steering tube is pushed against said clamp at a point distal from said common hinge region.

* * * * *